(12) United States Patent
Le Guern et al.

(10) Patent No.: US 7,569,565 B2
(45) Date of Patent: Aug. 4, 2009

(54) PHARMACEUTICAL COMPOSITION FOR THE PREVENTION OR TREATMENT OF CEREBRAL OEDEMAS

(75) Inventors: Marie-Emmanuelle Le Guern, Compiegne (FR); Philippe Girard, Margny-les-Compiegne (FR); Jean-Marie Gillardin, Jonquieres (FR); Laurence Berthon-Cedille, Ricquebourg (FR); Bernard Hublot, Compiegne (FR)

(73) Assignee: Biocodex, Gentilly (FR)

( * ) Notice: Subject to any disclaimer, the term of this patent is extended or adjusted under 35 U.S.C. 154(b) by 128 days.

(21) Appl. No.: 11/488,068

(22) Filed: Jul. 18, 2006

(65) Prior Publication Data

US 2007/0021415 A1    Jan. 25, 2007

(30) Foreign Application Priority Data

Jul. 19, 2005    (FR) .................................. 05 07649

(51) Int. Cl.
*A61K 31/536*    (2006.01)
(52) U.S. Cl. ................................... 514/230.5
(58) Field of Classification Search .............. 514/230.5, 514/266.1, 266.3, 266.31, 266.4
See application file for complete search history.

(56) References Cited

U.S. PATENT DOCUMENTS

2004/0209904 A1    10/2004    Dunn et al.

FOREIGN PATENT DOCUMENTS

DE    3439055    4/1986

OTHER PUBLICATIONS

Raslan et al., Medical management of cerebral edema, 2007, Neurosurg Focus, 22 (5):E12, pp. 1, 8 and 9.*
Verleye et al., Interactions of etifoxine with the chlorine channel coupled to the GABAA receptor complex, 1999, NeuroReport, 10, 3207-3210.*
Landolt, A.M. (1973), "Das Hirnodem," Therapeutische Umschau; vol. 30, No. 8, pp. 591-596; XP009063608.
Kruse H.J. et al. (1985) "Etifoxine: Evaluation of its Anticonvulsant Profile in Mice in Comparison with Sodium Valproate, Phenytoin and Clobazam," Arzneimittel-Forschung/Drug Research, vol. 35, No. 1, pp. 133-135; XP002372434; Database EMBASE [Online] Elsevier Science publishers, Amsterdam, NL (Abstract).
Kruse H.J. et al. (1986) "Potentiation of Clobazam's Anticonvulsant Activity by Etifoxine, a Non-Benzodiazepine Tranquilizer, in Mice. Comparison Studies with Sodium Valproate," Arzneimittel-Forschung/Drug Research, vol. 36, No. 9, pp. 1320-1322; Database EMBASE [Online] Elsevier Science publishers, Amsterdam, NL (Abstract).

* cited by examiner

*Primary Examiner*—Kamal A Saeed
*Assistant Examiner*—Kristin Bianchi
(74) *Attorney, Agent, or Firm*—B. Aaron Schulman; Stephen J. Weyer; Stites & Harbison PLLC

(57) ABSTRACT

The present invention relates to the use of at least one compound of formula (I) below:

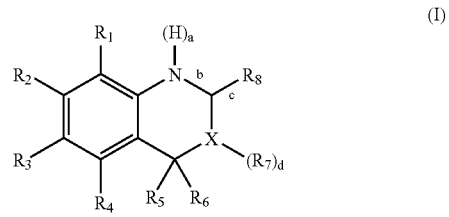

or of its pharmaceutically acceptable salts, in the preparation of a medicament for the prevention or treatment of cerebral oedemas.

8 Claims, 9 Drawing Sheets

PHARMACEUTICAL COMPOSITION FOR THE PREVENTION OR TREATMENT OF CEREBRAL OEDEMAS

The present invention relates to a pharmaceutical composition for the prevention or treatment of cerebral oedema.

Cerebral oedema is characterised as being an excessive accumulation of water in the intra- and/or extra-cellular compartments of the brain (Pollay (1996) in *Neurosurgery*, $2^{nd}$ ed. McGraw Hill Book Co., New York, 335-344). Cerebral oedema can be of neurological origin, as in the case of ischaemic attacks, intracerebral haemorrhages, brain turnouts or cases of meningitis or of encephalitis, or of non-neurological origin, as in the case of diabetic ketoacidosis, lactic acidosis, hypertensive encephalopathy, malignant hypertension, hyponatraemia or an effect of high altitude.

The principal consequence of cerebral oedema is an increase in the intracranial fluid pressure, leading to a reduction in the blood supply to the brain and the partial or total destruction of insufficiently vascularised cerebral tissues.

Few compounds are available for the pharmacological treatment of cerebral oedemas; among the most commonly used, the following compounds can be mentioned:

- mannitol, and to a lesser degree glycerol, are used as agents for osmotherapy; however, prolonged administration of mannitol leads to an electrolytic imbalance which can counterbalance its beneficial effects by causing, for example, cardiopulmonary troubles (Davis et al. (1994) *J. Neurosci. Nurs.* 26:170-174);
- diuretics, such as furosemide, are used only in controlled release to prolong the effect of osmotic agents;
- corticoids, especially glucocorticoids, such as dexamethasone, act principally on the blood vessels and are therefore indicated in particular in the case of cerebral oedemas of vascular origin; on the other hand, they are not recommended in the treatment of oedemas following ischaemias or haemorrhages; moreover, systemic complications associated with steroids can lead to a deterioration in the patient's condition (Rosenberg (2000) in *Neurology in clinical practice*, $3^{rd}$ ed. Butterworth Heinmann, Boston, 2:1545-1559);
- barbiturates, which are used less frequently than in the past, seem to act by causing a decrease in the level of metabolic activity; however, these compounds also cause systemic hypotension and pulmonary insufficiencies.

Etifoxine, or 6-chloro-2-ethylamino-4-methyl-4-phenyl-4H-[3,1]benzoxazine hydrochloride, belongs to the benzoxazine family. It promotes GABAergic transmission by binding to a receptor of the chlorine channel and is currently used as an anxiolytic. Few undesirable side-effects following its use are documented.

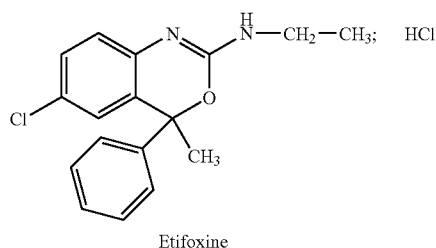

Etifoxine

The synthesis of that compound is described especially in French Patent No. 1 571 287. Moreover, several active metabolites of etifoxine have been described, such as des-ethyl-etifoxine or 2-amino-6-chloro-4-methyl-4-phenyl-4H-[3,1]benzoxazine, 6-chloro-4-hydroxyphenyl)-4-methyl-3,4-dihydro-1H-quinazolin-2-one or 6-chloro-3-ethyl-7-hydroxy-4-methyl-4-phenyl-3,4-dihydro-1H-quinazolin-2-one.

The object of the present invention is to provide novel compounds which do not have the disadvantages of the compounds already known, within the scope of the prevention or treatment of cerebral oedema.

As such, the present invention derives from the discovery by the inventors that etifoxine and its derivatives permit the prevention or treatment of cerebral oedema.

The present invention accordingly relates to the use of at least one compound of formula (I) below:

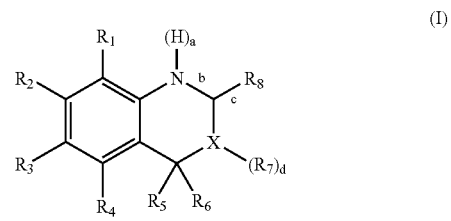

(I)

in which:
- a represents 0 or 1;
- b represents a single bond or a double bond;
- c represents a single bond or a double bond;
- d represents 0 or 1;
- X represents an oxygen atom or a nitrogen atom, with the proviso that when X represents an oxygen atom, d is 0, and when X represents a nitrogen atom, d is 1;
- $R_1$, $R_2$, $R_3$ and $R_4$, which may be identical or different, represent a hydrogen atom, a halogen atom, especially selected from F, Cl, Br and I, a hydroxyl group, or an alkoxy group having 1 or 2 carbon atoms;
- $R_5$ and $R_6$, which may be identical or different, represent a hydrogen atom, an alkyl or cycloalkyl group having from 1 to 6 carbon atoms, or an aryl group having 6 carbon atoms, the aromatic ring of which is optionally substituted by one or more halogen atoms or by one or more hydroxyl, alkoxy having 1 or 2 carbon atoms, trifluoromethyl or nitro groups;
- $R_7$ represents a hydrogen atom, a hydroxyl group, or an alkyl or hydroxyalkyl group having from 1 to 3 carbon atoms;
- $R_8$ represents an oxygen atom or a —$NR_9R_{10}$ group, $R_9$ and $R_{10}$, which may be identical or different, representing a hydrogen atom, a hydroxyl group, or an alkyl or hydroxyalkyl group having from 1 to 3 carbon atoms, with the proviso that when $R_8$ represents an oxygen atom, a is 1, b represents a single bond and c represents a double bond, and when $R_8$ represents a group —$NR_9R_{10}$, a is 0, b represents a double bond and c represents a single bond;

or of the pharmaceutically acceptable salts thereof, in the preparation of a medicament for the prevention or treatment of cerebral oedemas.

The term "cerebral oedemas" is used to denote conditions in which there is an excessive accumulation of water in the intra- and/or extra-cellular compartments of the brain. Cerebral oedemas are described especially in Pollay (1996) in *Neurosurgery*, 2$^{nd}$ ed. McGraw Hill Book Co., New York, 335-344.

The synthesis of the compounds of formula (I) defined hereinbefore can readily be carried out on the basis of the teachings of French Patent No. 1 571 287.

The activity of the compounds of formula (I) hereinbefore in the prevention or treatment of cerebral oedema can be verified, for example in an animal model, such as the rat, by measuring, after sacrifice, the significant decrease in the percentage of water in the brain of animals which have received triethyl tin and have been treated with the compounds of formula (I), by comparison with animals which have received triethyl tin and have not been treated. This test, described by Linee et al., 1984 *Ann. Pharm. Fr.* 42, 431-442, is carried out in the Examples.

Advantageously, the compounds of formula (I) hereinbefore are capable of acting according to a process different from that implemented by the compounds conventionally used within the scope of the treatment of cerebral oedema and therefore do not have their detrimental effects.

The pharmaceutically acceptable salts according to the invention will become apparent in an evident manner to the person skilled in the art; particular preference is given to the hydrochloride salts of the compounds of formula (I) according to the invention.

As it is understood here, the present invention relates also to the use, as defined hereinbefore, of the optically active forms of the compound of formula (I), such as the following enantiomers (when $R_5$ and $R_6$ are different):

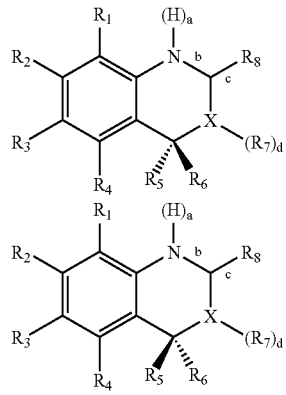

or mixtures thereof, especially the racemic mixture thereof.

In a particular embodiment, the invention relates to the use as defined hereinbefore of a compound of formula (VIII) below:

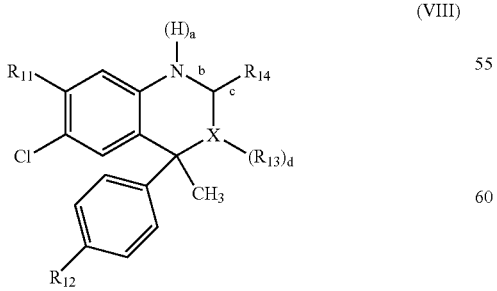

(VIII)

in which:

a represents 0 or 1;

b represents a single bond or a double bond;

c represents a single bond or a double bond;

d represents 0 or 1;

X represents an oxygen atom or a nitrogen atom, with the proviso that when X represents an oxygen atom, d is 0, and when X represents a nitrogen atom, d is 1;

$R_{11}$ and $R_{12}$, which may be identical or different, represent —H or —OH;

$R_{13}$ represents —H or a —CH$_2$—CH$_3$ group;

$R_{14}$ represents an oxygen atom or a —NH$_2$ or —NH—CH$_2$—CH$_3$ group, with the proviso that when $R_{14}$ represents an oxygen atom, a is 1, b represents a single bond and c represents a double bond, and when $R_{14}$ represents a —NH$_2$ or —NH—CH$_2$—CH$_3$ group, a is 0, b represents a double bond and c represents a single bond.

The present invention relates also to the use, as defined hereinbefore, of the optically active forms of the compound of formula (VIII), such as the following enantiomers:

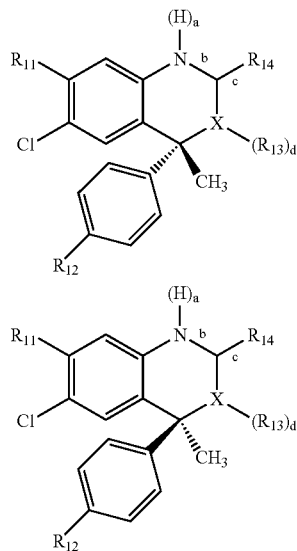

or mixtures thereof, in particular the racemic mixture thereof.

In a particular embodiment, the invention relates to the use, as defined hereinbefore, of a compound of formula (II) below:

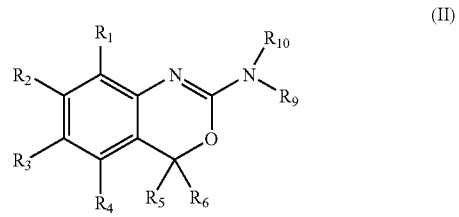

(II)

in which $R_1$, $R_2$, $R_3$, $R_4$, $R_5$, $R_6$, $R_9$ and $R_{10}$ are as defined hereinbefore.

The present invention relates also to the use, as defined hereinbefore, of the optically active forms of the compound of formula (II), such as the following enantiomers (when $R_5$ and $R_6$ are different):

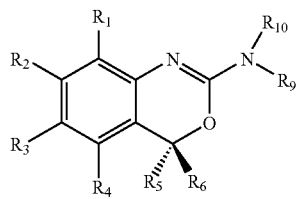

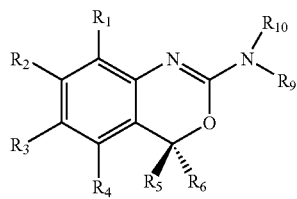

or mixtures thereof, in particular the racemic mixture thereof.

In another particular embodiment, the invention relates to the use, as defined hereinbefore, of the compounds of formulae (III) and (IV) below:

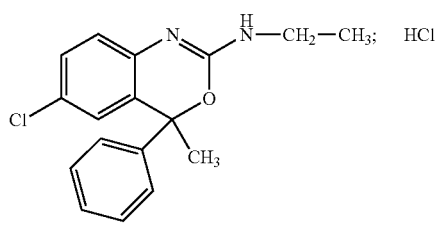

(III)

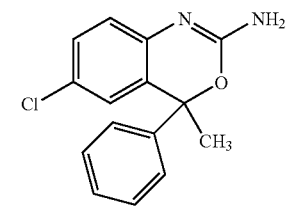

(IV)

The compound of formula (III) is etifoxine, or 6-chloro-2-ethylamino-4-methyl-4-phenyl-4H-[3,1]benzoxazine hydrochloride.

The compound of formula (IV), desethyl-etifoxine or 2-amino-6-chloro-4-methyl-4-phenyl-4H-[3,1]benzoxazine, is a metabolite of etifoxine.

The present invention relates also to the use, as defined hereinbefore, of the optically active forms of the compound of formula (III), such as the following enantiomers:

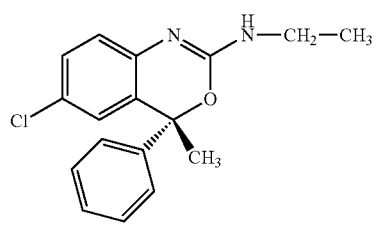

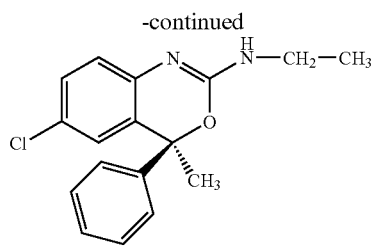

-continued or mixtures thereof, in particular the racemic mixture thereof, especially in the form of the hydrochloride, and to the use, as defined hereinbefore, of the optically active forms of the compound of formula (IV), such as the following enantiomers:

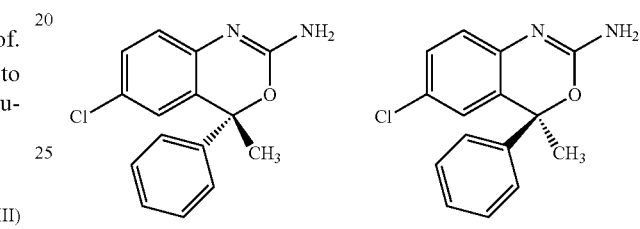

or mixtures thereof, in particular the racemic mixture thereof.

In another embodiment, the invention relates to the use, as defined hereinbefore, of a compound of formula (V) below:

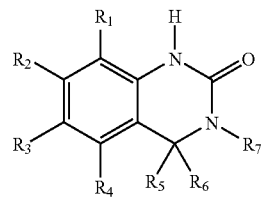

(V)

in which $R_1$, $R_2$, $R_3$, $R_5$, $R_6$, and $R_7$ are as defined hereinbefore.

The present invention relates also to the use, as defined hereinbefore, of the optically active forms of the compound of formula (V), such as the following enantiomers (when $R_5$ and $R_6$ are different):

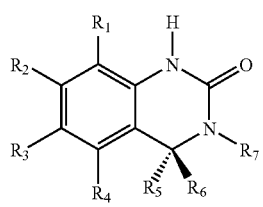 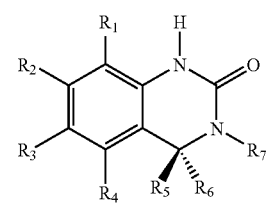

or mixtures thereof, in particular the racemic mixture thereof.

In another particular embodiment, the invention relates to the use, as defined hereinbefore, of compounds of formulae (VI) and (VII) below:

(VI)

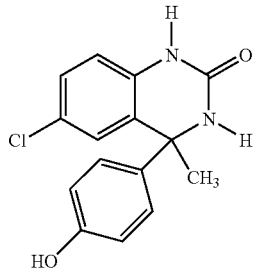

(VII)

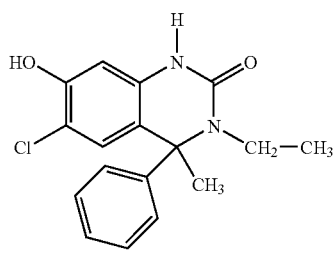

The compounds of formulae (VI) (6-chloro-4-(4-hydroxyphenyl)-4-methyl-3,4-dihydro-1H-quinazolin-2-one) and (VII) (6-chloro-3-ethyl-7-hydroxy-4-methyl-4-phenyl-3,4-dihydro-1H-quinazolin-2-one) are metabolites of etifoxine.

The present invention relates also to the use, as defined hereinbefore, of the optically active forms of the compound of formula (VI), such as the following enantiomers:

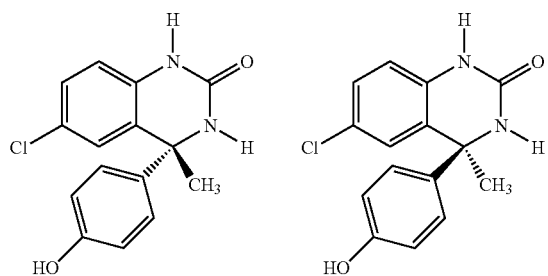

or mixtures thereof, in particular the racemic mixture thereof, and to the use, as defined hereinbefore, of the optically active forms of the compound of formula (VII), such as the following enantiomers:

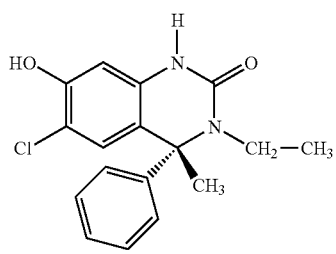

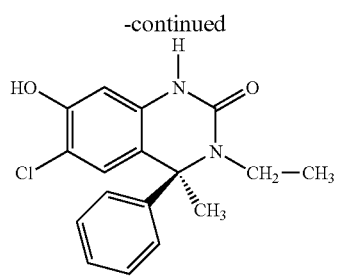

or mixtures thereof, in particular the racemic mixture thereof.

According to a particular embodiment of the use as defined hereinbefore, the cerebral oedema follows a cerebral vascular accident, a cerebral trauma, a cerebral tumour, cerebral metastases of a cancer, a cerebral abscess, a hypertensive attack, a diabetic ketoacidosis or a neuropaludism.

In a particular embodiment of the invention, the medicament defined hereinbefore is suitable for administration to an individual in need thereof of a dose of from approximately 50 mg to approximately 1500 mg, especially from approximately 150 to approximately 200 mg, of the compound as defined hereinbefore.

In a particular embodiment of the invention, the medicament defined hereinbefore is suitable for administration to an individual in need thereof of a dose of from approximately 50 mg/day to approximately 1500 mg/day, especially from approximately 150 mg/day to approximately 200 mg/day, of the compound as defined hereinbefore.

According to another preferred embodiment, the medicament defined hereinbefore is suitable for oral administration.

According to a preferred embodiment of the invention, the medicament defined hereinbefore is in the form of a powder, tablets, capsules or sachets.

In another particular embodiment of the use as defined hereinbefore, the compound defined hereinbefore is associated with at least one additional compound for the prevention or treatment of cerebral oedema, such as a compound selected from the group comprising a corticoid, especially a glucocorticoid, glycerol, mannitol, a diuretic, especially furosemide, a barbiturate, tetracosactide, an antibiotic, CDP-choline (cytidine 5'-diphosphocholine), vinpocetine, a calcium inhibitor and a NMDA (N-methyl-D-aspartate) antagonist.

Advantageously, the association of a compound of formula (I), or its pharmaceutically acceptable salts, with an additional compound indicated in the treatment of cerebral oedema enables the dose or duration of administration of said additional compound to be reduced and accordingly the side-effects thereof to be limited.

The present invention relates also to a pharmaceutical composition comprising as active ingredient at least one compound of formula (I) as defined hereinbefore, or a pharmaceutically acceptable salt thereof, and at least one additional compound for the prevention or treatment of cerebral oedema, such as a compound selected from the group comprising a corticoid, especially a glucocorticoid, glycerol, mannitol, a diuretic, especially furosemide, a barbiturate, tetracosactide, an antibiotic, CDP-choline, vinpocetine, a calcium inhibitor and a NMDA antagonist, in association with a pharmaceutically acceptable carrier.

The present invention relates also to products comprising:
at least one compound of formula (I) as defined hereinbefore, or a pharmaceutically acceptable salt thereof, and at least one additional compound for the prevention or treatment of cerebral oedema, such as a compound selected from the list comprising a corticoid, especially a glucocorticoid, glycerol, mannitol, a diuretic, especially furosemide, a barbiturate, tetracosactide, an antibiotic, CDP-choline, vinpocetine, a calcium inhibitor and a NMDA antagonist, as a combination product for simultaneous, separate or sequential use for the prevention or treatment of cerebral oedema.

DESCRIPTION OF THE FIGURES

FIGS. 1A and 1B show the effect of etifoxine on cerebral oedema induced by triethyl tin (TET) in the rat, measured by the percentage of water in the brain (y axis). The rats are distributed in groups of 10 individuals and are treated over 5 days (from d0 to d4).

FIG. 1A: the rats receive neither TET nor etifoxine (−; −), TET in the absence of etifoxine (+; −), etifoxine at a rate of 50 mg/kg twice daily in the absence of TET (−; +), or TET (3 mg/kg/d) in the presence of etifoxine at a rate of 50 mg/kg twice daily (+; +).

FIG. 1B: the rats receive neither TET nor etifoxine (−; −), TET in the absence of etifoxine (+; −), etifoxine at a rate of 100 mg/kg twice daily in the absence of TET (−; +), or TET (3 mg/kg/d) in the presence of etifoxine at a rate of 100 mg/kg twice daily (+; +).

The star symbol (*) represents a significant difference with respect to the groups without treatment ($p<0.05$, ANOVA).

FIG. 2A, FIG. 2B

Figure 2A:
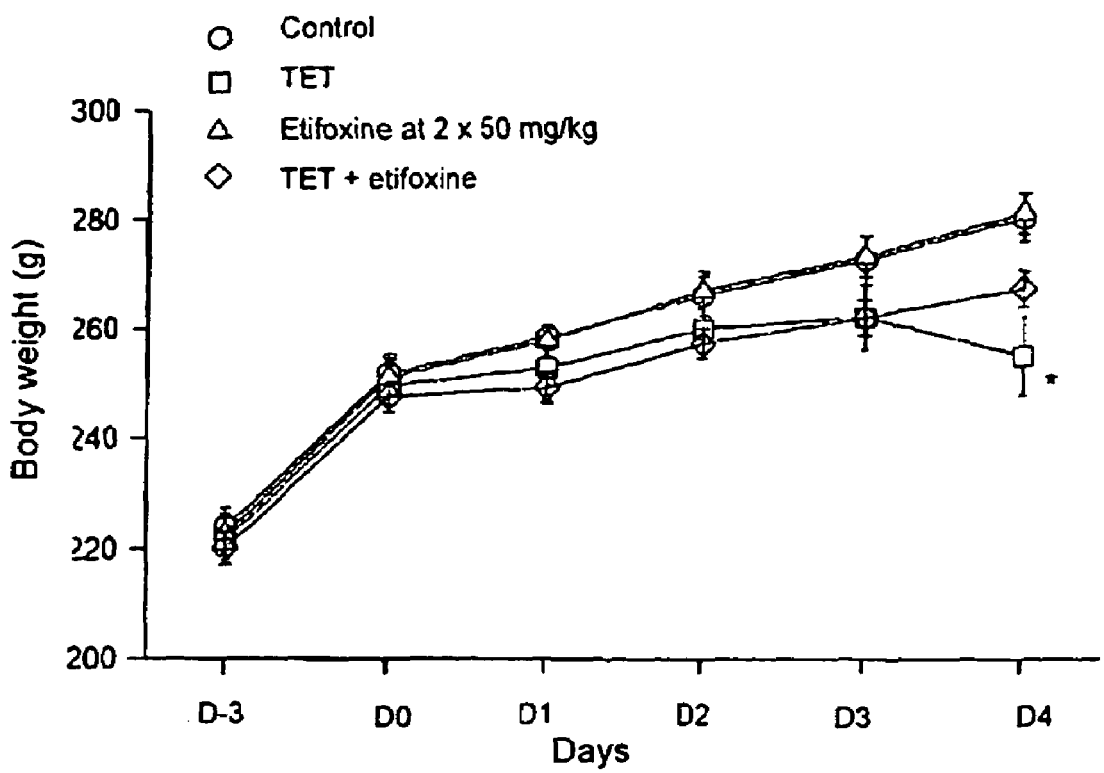
Figure 2B:
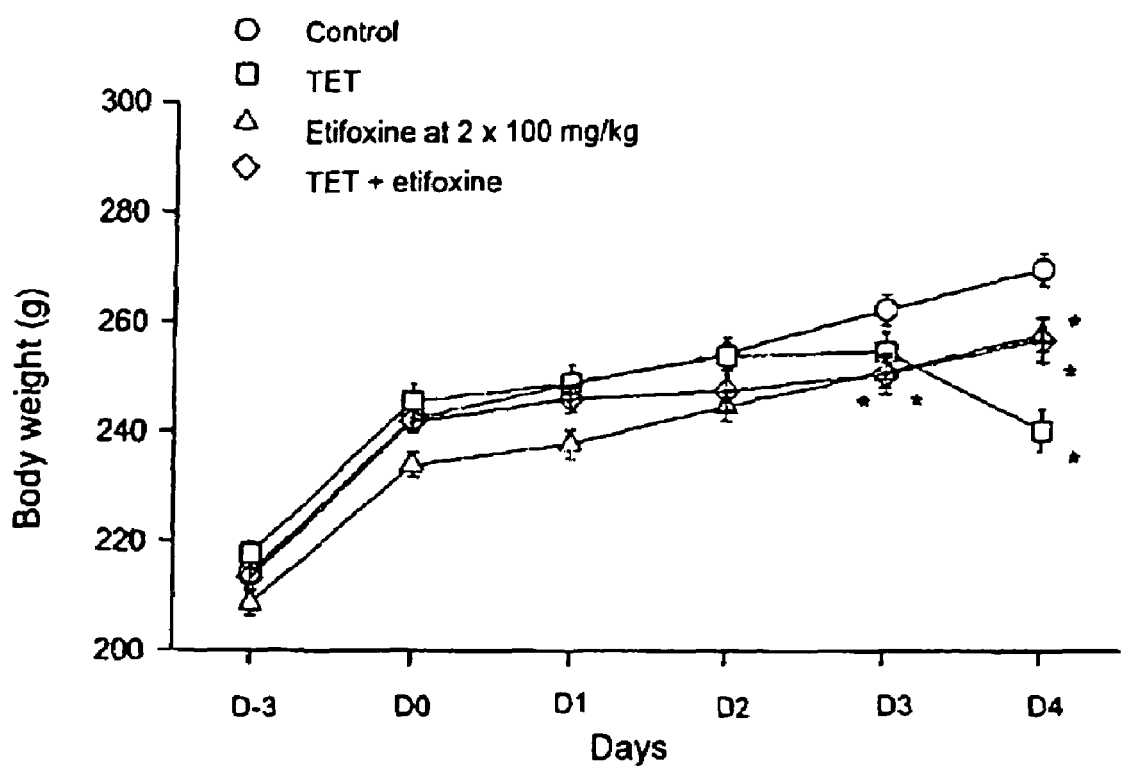

FIGS. 2A and 2B show the effect of etifoxine on the development of the body weight disrupted by triethyl tin in the rat (y axis, in grams) as a function of time (x axis, in days). The rats are distributed in groups of 10 individuals and are treated over 5 days (from d0 to d4).

FIG. 2A: the rats receive neither TET nor etifoxine (circles), TET in the absence of etifoxine (squares), etifoxine at a rate of 50 mg/kg twice daily in the absence of TET (triangles), or TET (3 mg/kg/d) in the presence of etifoxine at a rate of 50 mg/kg twice daily (diamonds).

FIG. 2B: the rats receive neither TET nor etifoxine (circles), TET in the absence of etifoxine (squares), etifoxine at a rate of 100 mg/kg twice daily in the absence of TET (triangles), or TET (3 mg/kg/d) in the presence of etifoxine at a rate of 100 mg/kg twice daily (diamonds).

The star symbol (*) represents a significant difference with respect to the respective control groups ($p<0.05$, ANOVA).

FIG. 3A, FIG. 3B

Figure 3A:
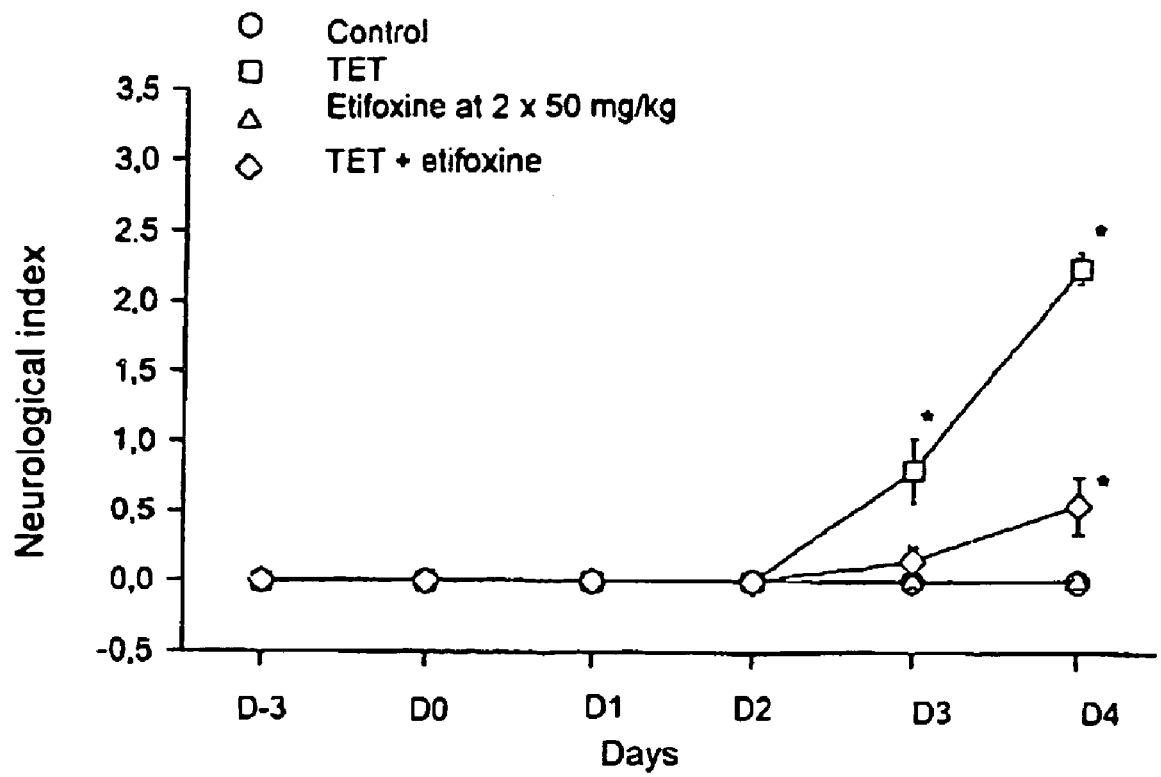
Figure 3B:
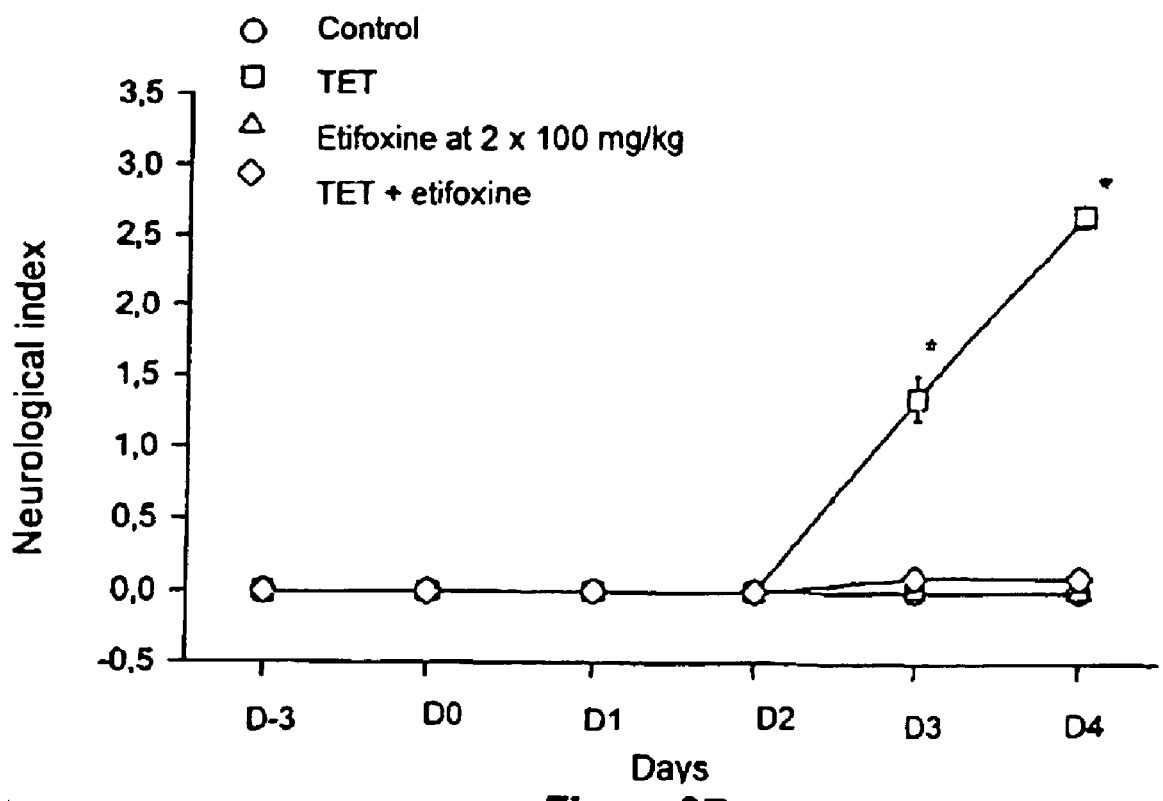

FIGS. 3A and 3B show the effect of etifoxine on the neurological index disrupted by triethyl tin in the rat (y axis) as a function of time (x axis, in days). The rats are distributed in groups of 10 individuals and are treated over 5 days (from d0 to d4).

FIG. 3A: the rats receive neither TET nor etifoxine (circles), TET in the absence of etifoxine (squares), etifoxine at a rate of 50 mg/kg twice daily in the absence of TET (triangles), or TET (3 mg/kg/d) in the presence of etifoxine at a rate of 50 mg/kg twice daily (diamonds).

FIG. 3B: the rats receive neither TET nor etifoxine (circles), TET in the absence of etifoxine (squares), etifoxine at a rate of 100 mg/kg twice daily in the absence of TET (triangles), or TET (3 mg/kg/d) in the presence of etifoxine at a rate of 100 mg/kg twice daily (diamonds).

The star symbol (*) represents a significant difference with respect to the respective control groups ($p<0.05$, ANOVA).

FIG. 4A, FIG. 4B, FIG. 4C

Figure 4A:
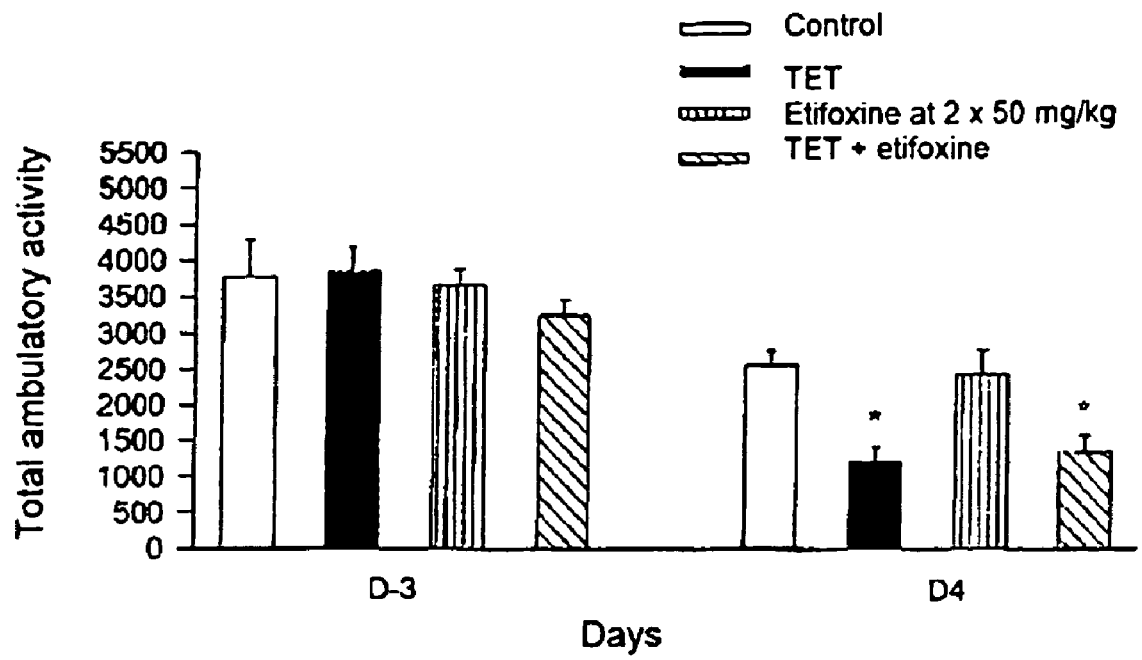
Figure 4B:
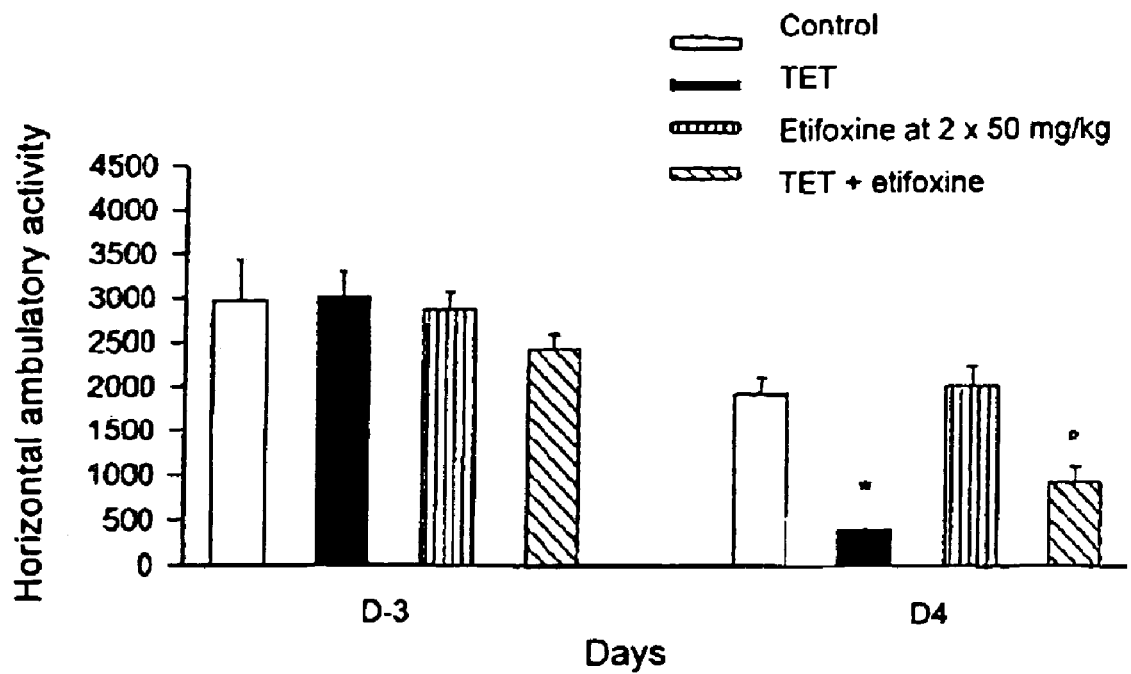
Figure 4C:
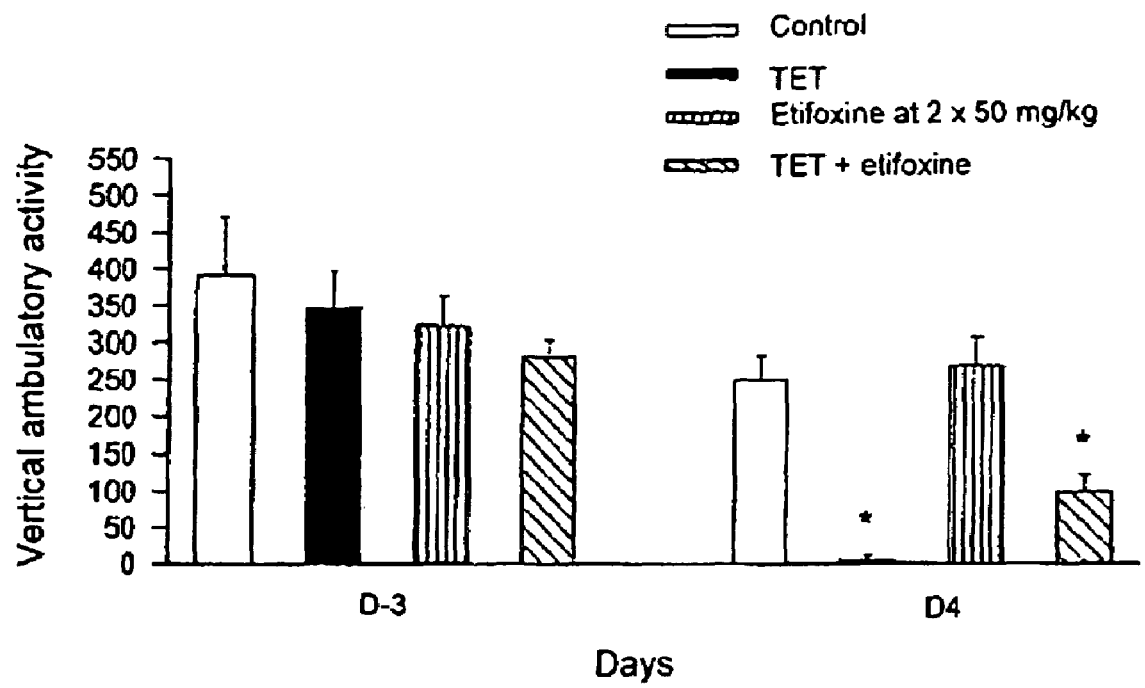

FIGS. 4A, 4B and 4C respectively show the effect of etifoxine on the total ambulatory activity (y axis, arbitrary units) (FIG. 4A), on the horizontal ambulatory activity (FIG. 4B) or on the vertical ambulatory activity (FIG. 4C) disrupted by triethyl tin in the rat, three days before any treatment (d-3) or 5 days after the start of treatment (d4). The rats are distributed in groups of 10 individuals and are treated over 5 days (from d0 to d4).

The rats receive neither TET nor etifoxine (white column), TET in the absence of etifoxine (black column), etifoxine at a rate of 50 mg/kg twice daily in the absence of TET (vertically hatched column), or TET (3 mg/kg/d) in the presence of etifoxine at a rate of 50 mg/kg twice daily (diagonally hatched column).

The star symbol (*) represents a significant difference with respect to the respective control groups ($p<0.05$, ANOVA).

FIG. 5A, FIG. 5B, FIG. 5C

Figure 5A:
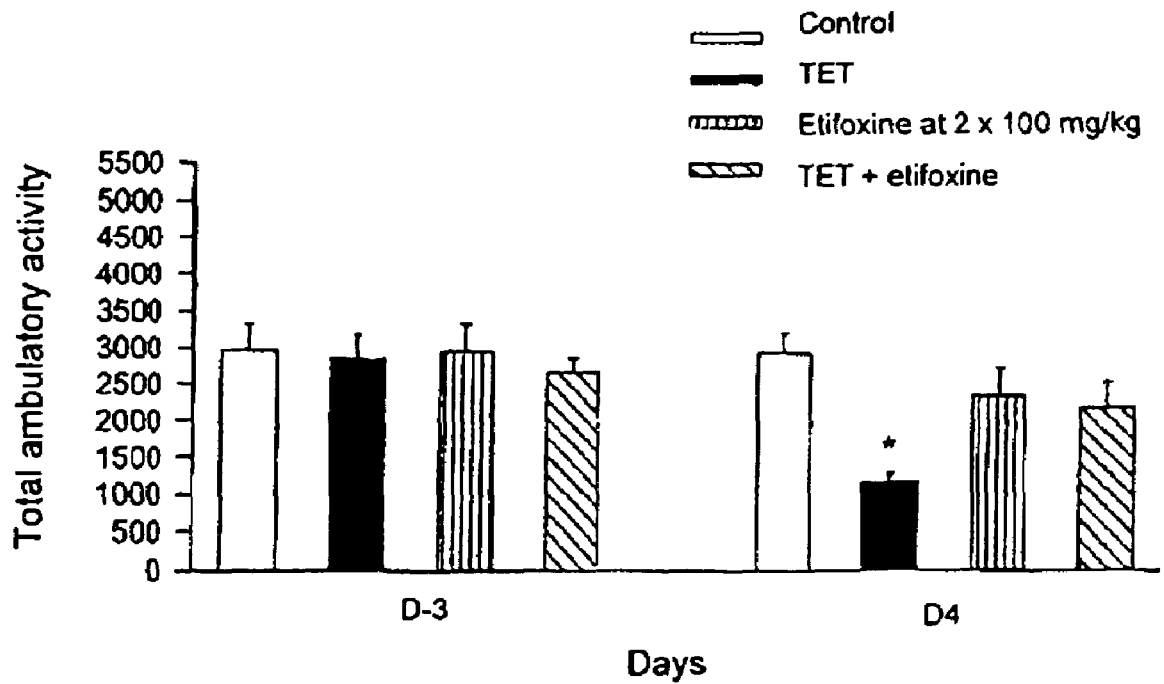
Figure 5B:
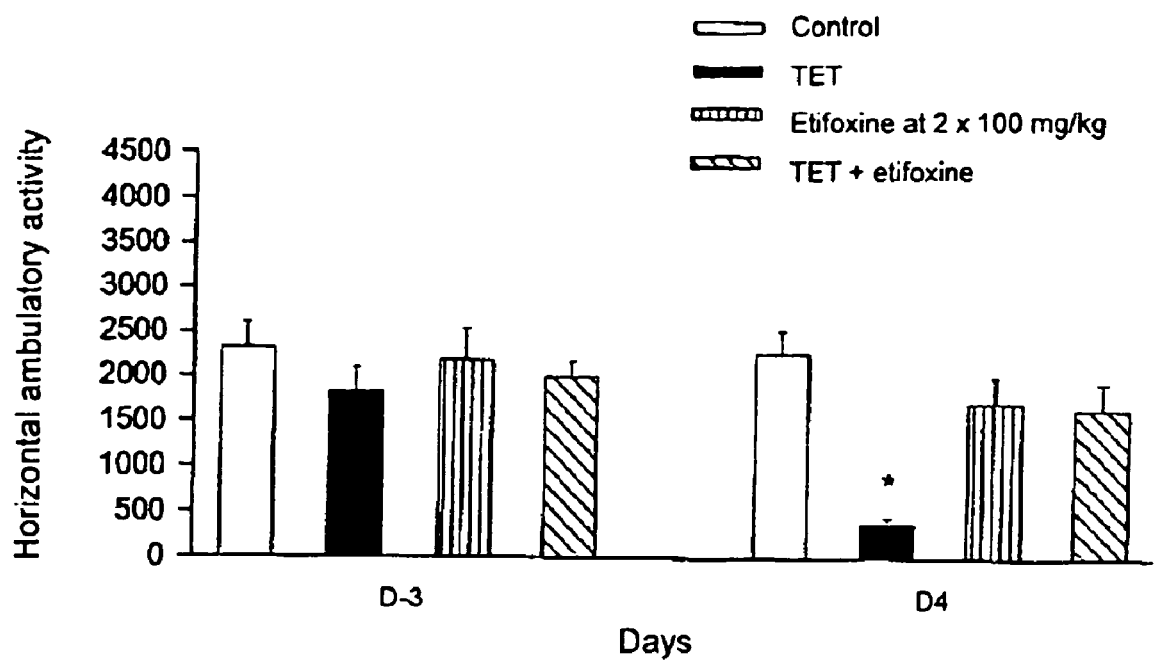
Figure 5C:
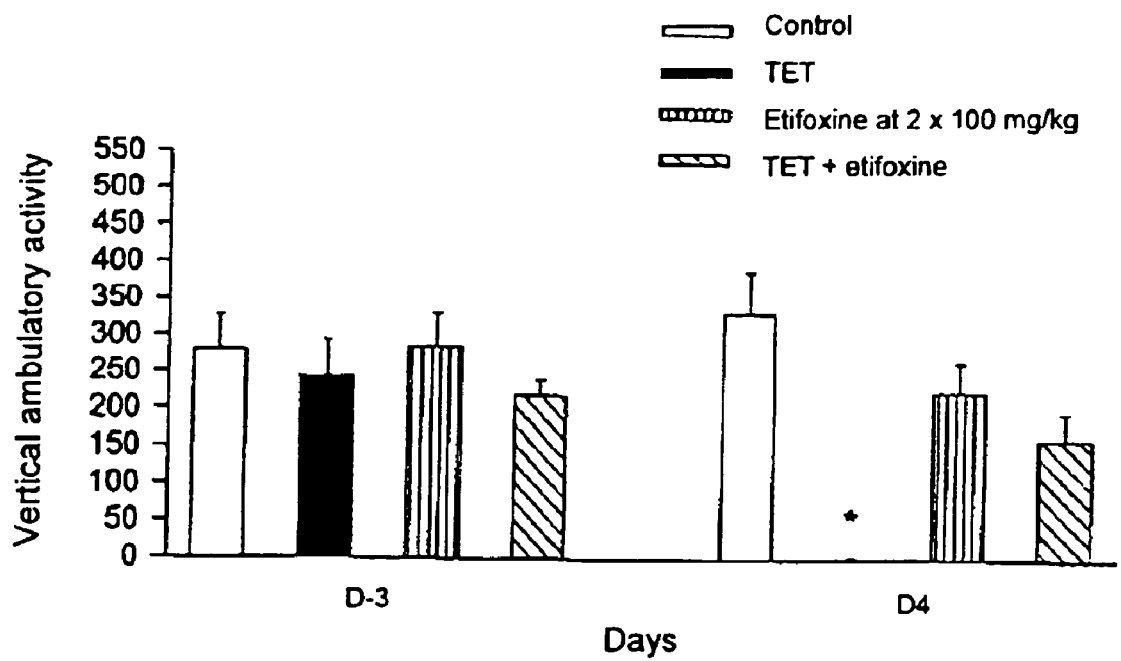

FIGS. 5A, 5B and 5C respectively show the effect of etifoxine on the total ambulatory activity (y axis, arbitrary units) (FIG. 5A), on the horizontal ambulatory activity (FIG. 5B) or on the vertical ambulatory activity (FIG. 5C) disrupted by triethyl tin in the rat, three days before any treatment (d-3) or 5 days after the start of treatment (d4). The rats are distributed in groups of 10 individuals and are treated over 5 days (from d0 to d4).

The rats receive neither TET nor etifoxine (white column), TET in the absence of etifoxine (black column), etifoxine at a rate of 100 mg/kg twice daily in the absence of TET (vertically hatched column), or TET (3 mg/kg/d) in the presence of etifoxine at a rate of 100 mg/kg twice daily (diagonally hatched column).

The star symbol (*) represents a significant difference with respect to the respective control groups ($p<0.05$, ANOVA).

FIG. 6

Figure 6:
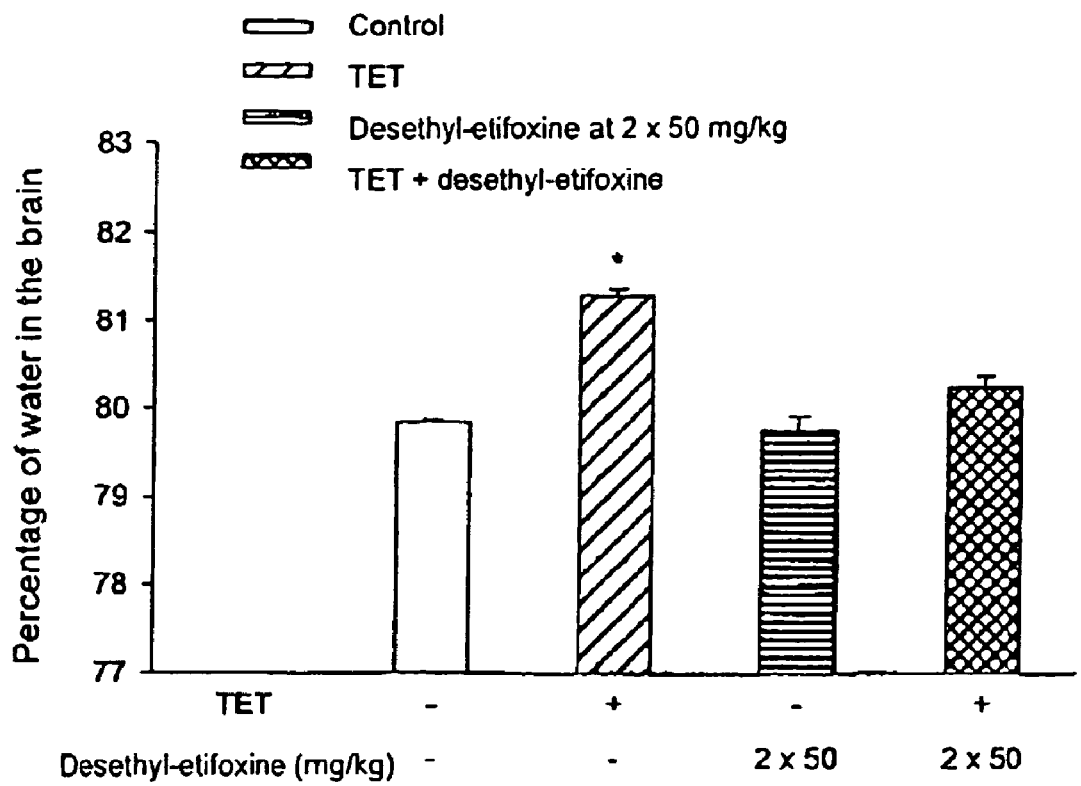

FIG. 6 shows the effect of desethyl-etifoxine on cerebral oedema induced by triethyl tin (TET) in the rat, measured by the percentage of water in the brain (y axis). The rats are distributed in groups of 10 individuals and are treated over 5 days (from d0 to d4).

The rats receive neither TET nor desethyl-etifoxine (−; −), TET (3 mg/kg/d) in the absence of desethyl-etifoxine (+; −), desethyl-etifoxine at a rate of 50 mg/kg twice daily in the absence of TET (−; +), or TET (3 mg/kg/d) in the presence of desethyl-etifoxine at a rate of 50 mg/kg twice daily (+; +).

The star symbol (*) represents a significant difference with respect to the groups without treatment ($p<0.05$, ANOVA).

FIG. 7

Figure 7:
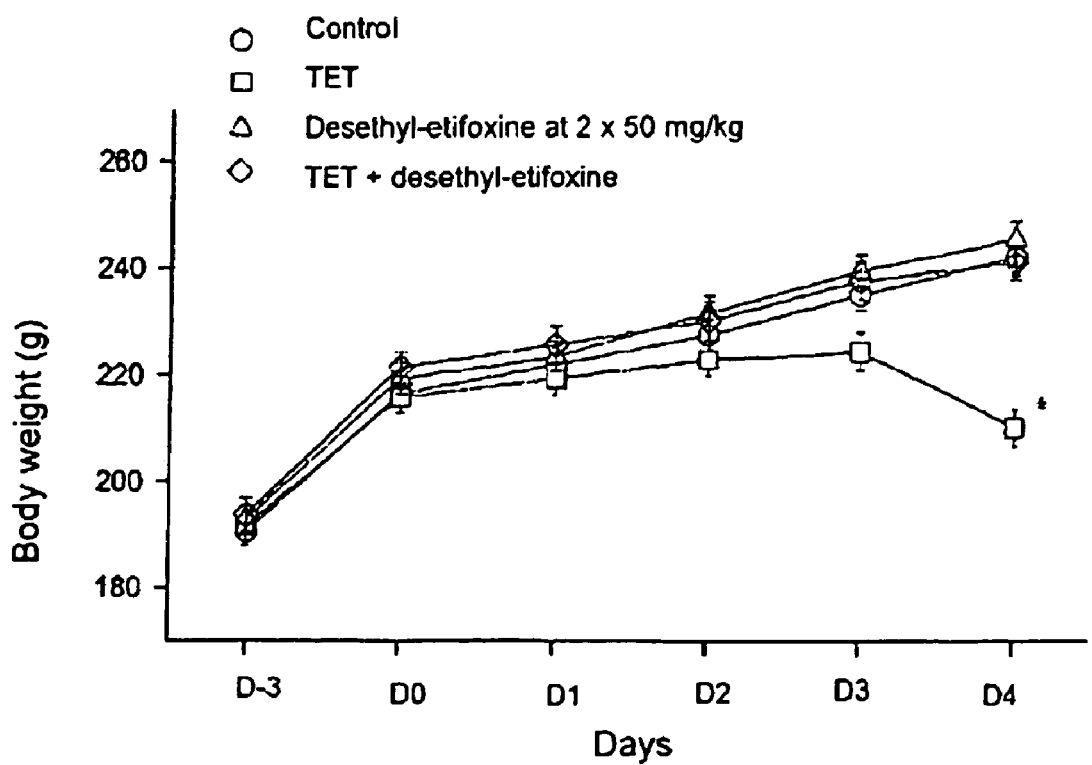

FIG. 7 shows the effect of desethyl-etifoxine on the development of the body weight disrupted by triethyl tin in the rat (y axis, in grams) as a function of time (x axis, in days). The rats are distributed in groups of 10 individuals and are treated over 5 days (from d0 to d4).

The rats receive neither TET nor desethyl-etifoxine (circles), TET (3 mg/kg/d) in the absence of desethyl-etifoxine (squares), desethyl-etifoxine at a rate of 50 mg/kg twice daily in the absence of TET (triangles), or TET (3 mg/kg/d) in the presence of desethyl-etifoxine at a rate of 50 mg/kg twice daily (diamonds).

The star symbol (*) represents a significant difference with respect to the groups without treatment ($p<0.05$, ANOVA).

FIG. 8

Figure 8:
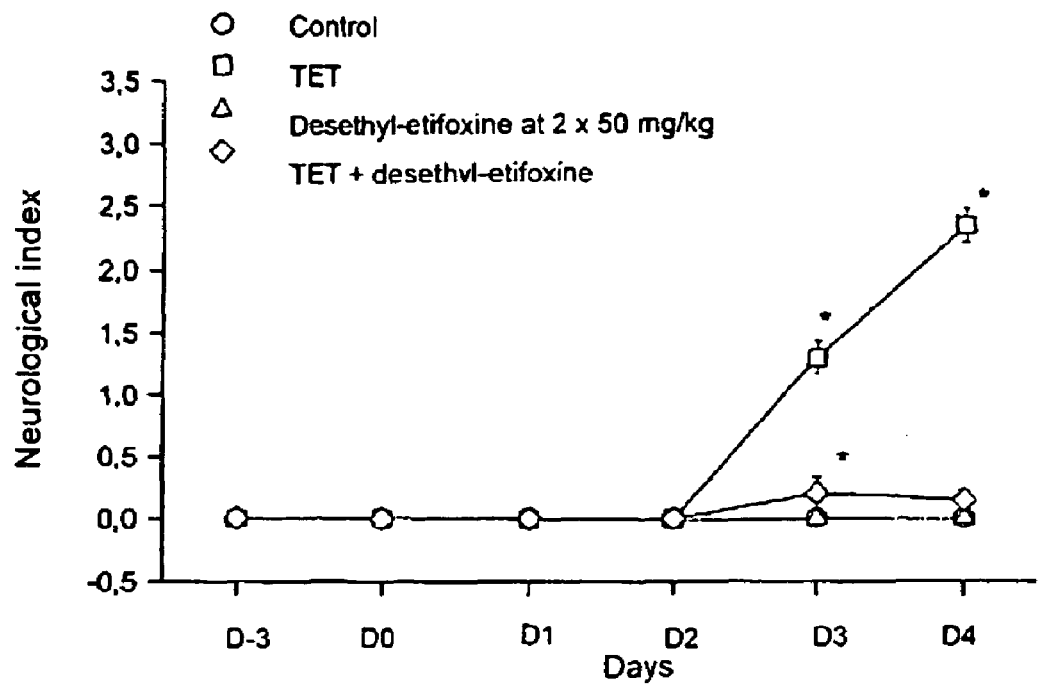

FIG. 8 shows the effect of desethyl-etifoxine on the neurological index disrupted by triethyl tin in the rat (y axis) as a function of time (x axis, in days). The rats are distributed in groups of 10 individuals and are treated over 5 days (from d0 to d4).

The rats receive neither TET nor desethyl-etifoxine (circles), TET (3 mg/kg/d) in the absence of desethyl-etifoxine (squares), desethyl-etifoxine at a rate of 50 mg/kg twice daily in the absence of TET (triangles), or TET (3 mg/kg/d) in the presence of desethyl-etifoxine at a rate of 50 mg/kg twice daily (diamonds).

The star symbol (*) represents a significant difference with respect to the groups without treatment (p<0.05, ANOVA).

FIG. 9A, FIG. 9B, FIG. 9C

Figure 9A:
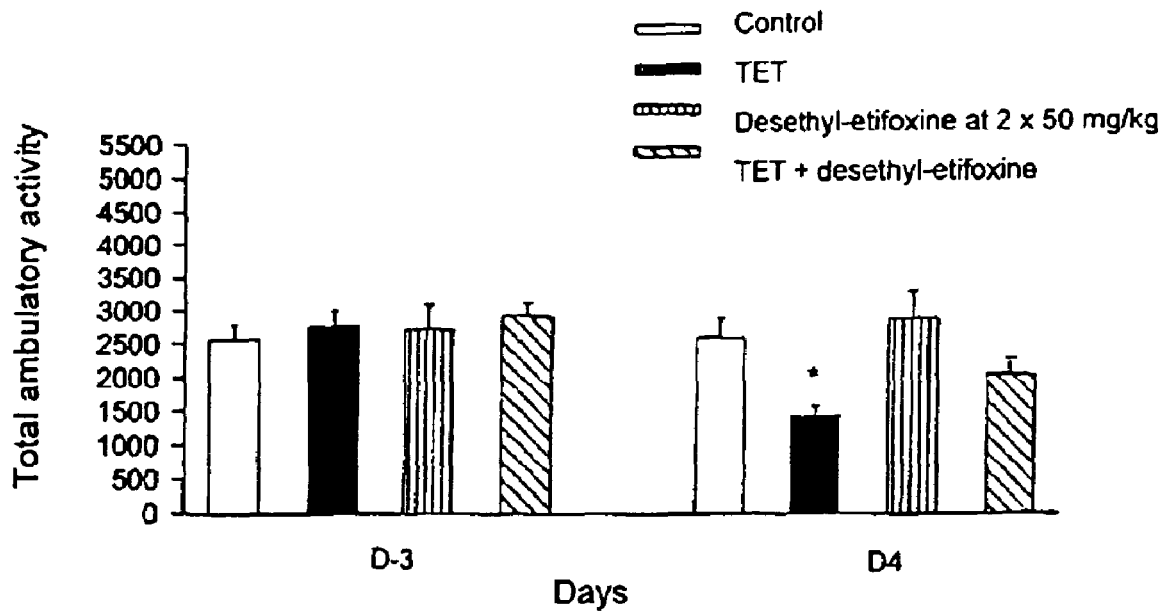
Figure 9B:
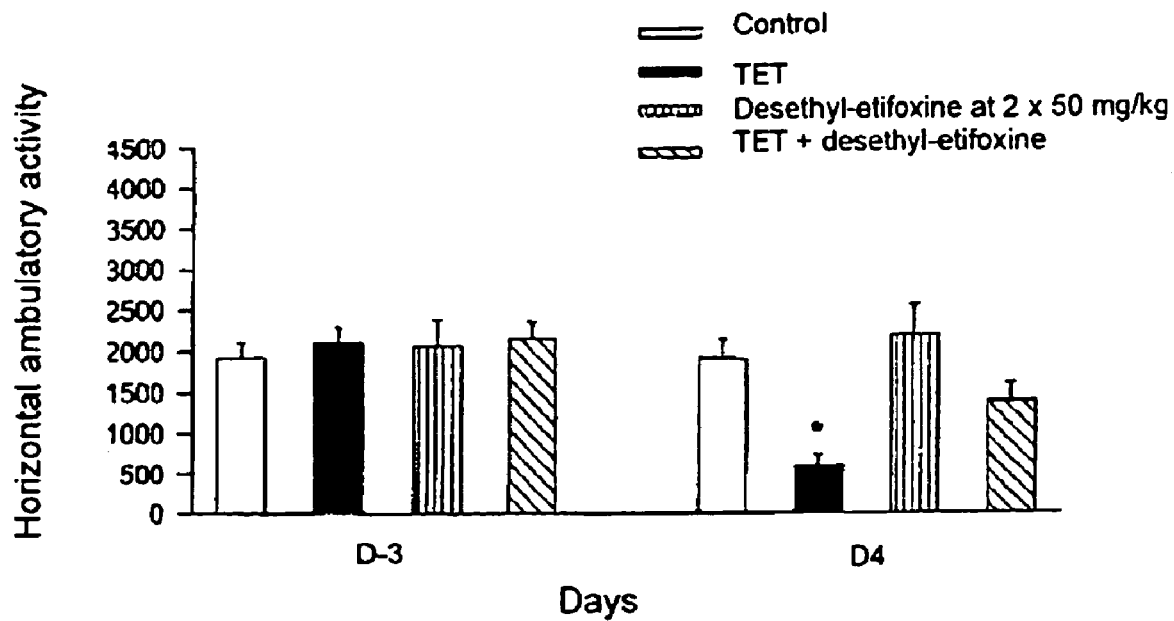
Figure 9C:
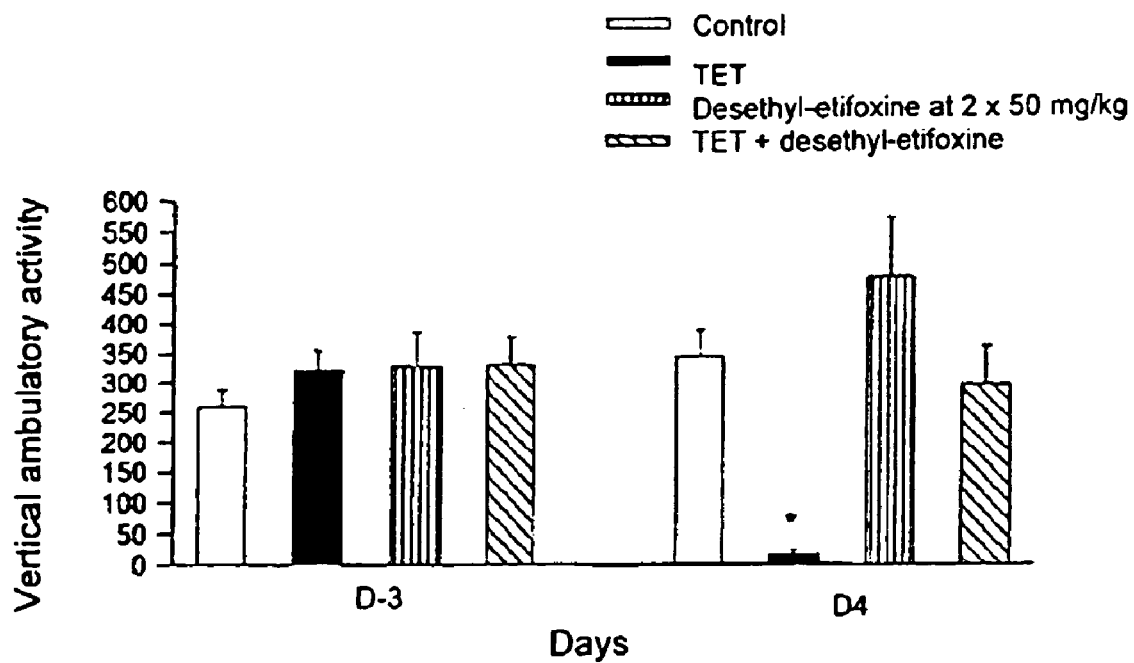

FIG. 9A, FIG. 9B and FIG. 9C show the effect of desethyl-etifoxine on the total ambulatory activity (y axis, arbitrary units) (FIG. 9A), on the horizontal ambulatory activity (FIG. 9B) or on the vertical ambulatory activity (FIG. 9C) disrupted by triethyl tin in the rat, three days before any treatment (d-3) or 5 days after the start of treatment (d4). The rats are distributed in groups of 10 individuals and are treated over 5 days (from d0 to d4).

The rats receive neither TET nor desethyl-etifoxine (white column), TET (3 mg/kg/d) in the absence of desethyl-etifoxine (black column), desethyl-etifoxine at a rate of 50 mg/kg twice daily in the absence of TET (vertically hatched column), or TET (3 mg/kg/d) in the presence of desethyl-etifoxine at a rate of 50 mg/kg twice daily (diagonally hatched column).

The star symbol (*) represents a significant difference with respect to the groups without treatment (p<0.05, ANOVA).

EXAMPLES

The inventors have demonstrated a protective effect of etifoxine on cerebral oedema induced by triethyl tin (TET) chloride. Moreover, the effect of etifoxine has also been studied on the disruptions induced by TET for the following 3 parameters: weight development, neurological index and ambulatory activity.

1. Materials and Methods 1.1. Model

Cerebral oedema induced by triethyl tin (TET) chloride in the rat is a physiopathological model for the study of substances recommended in the treatment of certain cerebrovascular disorders (Linee et al., 1984 *Ann. Pharm. Fr.* 42, 431-442). Intoxication with TET is also a useful toxicological tool for testing products which act at cerebral level in the elderly for testing new products in senescence (Bentue-Ferer et al., 1985 *Exp. Aging Res.* 11, 137-141)

Cerebral oedema due to TET is a chronic oedema which appears gradually and is spontaneously reversible on condition that the intoxication is stopped. The oedema develops exclusively at the level of the brain and of the spinal cord. Cerebral oedema is characterised by an increase in the contents of water, sodium and chlorides without significant modification of the potassium content. The oedema is reflected in a specific attack on the white matter (Naruse et al., 1982 *J. Neurosurg.* 56, 747-752), with a widening of the intramyelinic spaces and attack on the myelin (Kirschner and Sapirstein, 1982 *J. Neurocytol.* 11, 559-569). The myelin of the central nervous system has the potential to recover its integrity after oedematous damage by the withdrawal of the accumulated fluid (Yanagisawa et al., 1990 *Neurochem. Res.* 15, 483-486). The scale of the oedema, which is accompanied by a weight loss and by peripheral neurological disorders, is proportional to the dose of TET.

It has been demonstrated in particular that:
the administration of TET (bromide) at 1 mg/kg/d intraperitoneally for 7 days in the rat increases the percentage of water in the white matter (from 78% to 82%) but not in the grey matter (Naruse et al., 1982 *J. Neurosurg.* 56, 747-752);

the administration of TET (hydrochloride) in drinking water at 2-3% for 15 days in the rat increases the percentage of water from 78.0% to 80.0% (Borzeix and Cahn, 1984 *Int. J. Clin. Pharmacol. Res.* 4, 259-261);

the administration of TET (chloride) at 2 mg/kg/d orally for 5 days in the rat increases the percentage of water from 76-77% to 79-80% (Linee et al., 1984 *Ann. Pharm. Fr.* 42, 431-442);

the administration of TET (chloride) at 0.002% in drinking water for 14 days in the rat increases the percentage of water from 78.3% to 81.1% (Otani et al., 1986 *Acta Neuropathol.* (Berl) 69, 54-65).

According to a preventive protocol, the substances to be tested are administered during the intoxication with tin and their activities are measured after 5 days. Under those conditions, it has been shown that some cerebrovascular medicaments are active, such as dihydroergotoxin, (−) eburnamonine and vincamine (Linee et al., 1984 *Ann. Pharm. Fr.* 42, 431-442).

1.2. Animals

Male Wistar rats from Janvier weighing between 200 and 250 grams at the start of the experiment are used after at least 7 days acclimatisation in the animal house (t° ambient=22±2° C.; relative humidity=50±20% nutrition UAR "A04"; nyethemeral cycle (12 h/12 h (7.00 a.m.-7.00 p.m./7.00 p.m.-7.00 a.m.)).

1.3. Experimental Protocol

The protocol was adapted according to Linee et al. (Linee et al., 1984 *Ann. Pharm. Fr.* 42, 431-442):

at d-3, the rats are distributed randomly in cages (5 rats per cage);

triethyl tin is administered orally for 5 days (from d0 to d4) at about 8.00-8.30 a.m.;

the test product is given orally twice daily for 5 days (from d0 to d4) at about 9.00-9.30 a.m. and 4.00 p.m.;

the body weight and the neurological index are noted every day;

the ambulatory activity is measured at d-3, before any treatment, and at d4, at the end of the study;

as soon as the measurements are complete, the rat is sacrificed by decapitation and its brain is removed; each brain is weighed (fresh weight) and is then placed in an oven in order to obtain its dry weight.

1.4. Expression of the Results

Water Content of the Brain

The brain is weighed after removal in order to obtain the fresh weight.

The brain is then placed in an oven for drying to constant weight at 90° C. for 72 hours, in order to obtain the dry weight.

The percentage of water in each brain is then calculated.

Neurological Index: According to the Following 4 Criteria

0: no apparent anomaly

1: loss of spontaneous activity: the rat does not leave a limited surface within a period of 60 seconds, but it escapes normally therefrom if it is stimulated (noise, pinching); it has lost its exploratory activity but retains its motor capacities.

2: loss of gripping reflex when the rat is pushed against the surface.

3: loss of retreat reflex, coma followed in the majority of cases by death.

Ambulatory Activity

The motor activity is detected with the aid of 15 photoelectric cells distributed over the walls of the rectangular compartment (320×290×100 mm) of the Opto-Varimex system from Colombus Instruments U.S.A.

The number of displacements (ambulatory activities, horizontal and vertical) of the animal is counted for 15 minutes. The activity is expressed in arbitrary units: 1 unit corresponds to a passage in front of a photoelectric cell.

1.5. Products

Triethyl tin bromide at 97% (Sigma, ref 288047) is diluted in distilled water.

Etifoxine and desethyl-etifoxine are suspended in 1% Tween 80 and administered in a volume of 0.5 ml per 100 g body weight.

1.6. Statistics

The statistical test used is the analysis of variance (ANOVA). When the result does not depend upon chance (to 5%), the treated groups that differ from the control group are determined.

2. Results 2.1. Effect of the Dose of Triethyl Tin

Several doses of TET were studied in order to determine a dose enabling reproducible results to be obtained.

The administration of TET at 2 mg/kg/d orally has little effect at the level of the development of the body weight of the rats, or at the level of neurological index.

The administration of TET at 3 mg/kg/d causes a decrease in the body weight of the rats and signs of neurological toxicity from the $4^{th}$ day, but no mortality.

The administration of TET at 4 mg/kg/d leads to signs of neurological toxicity from the $2^{nd}$ day, and mortality from the $4^{th}$ day.

Consequently, a dose of 3 mg/kg/d was chosen for the following studies.

2.2. Effect of Etifoxine

Cerebral Oedema

Figure 1A:
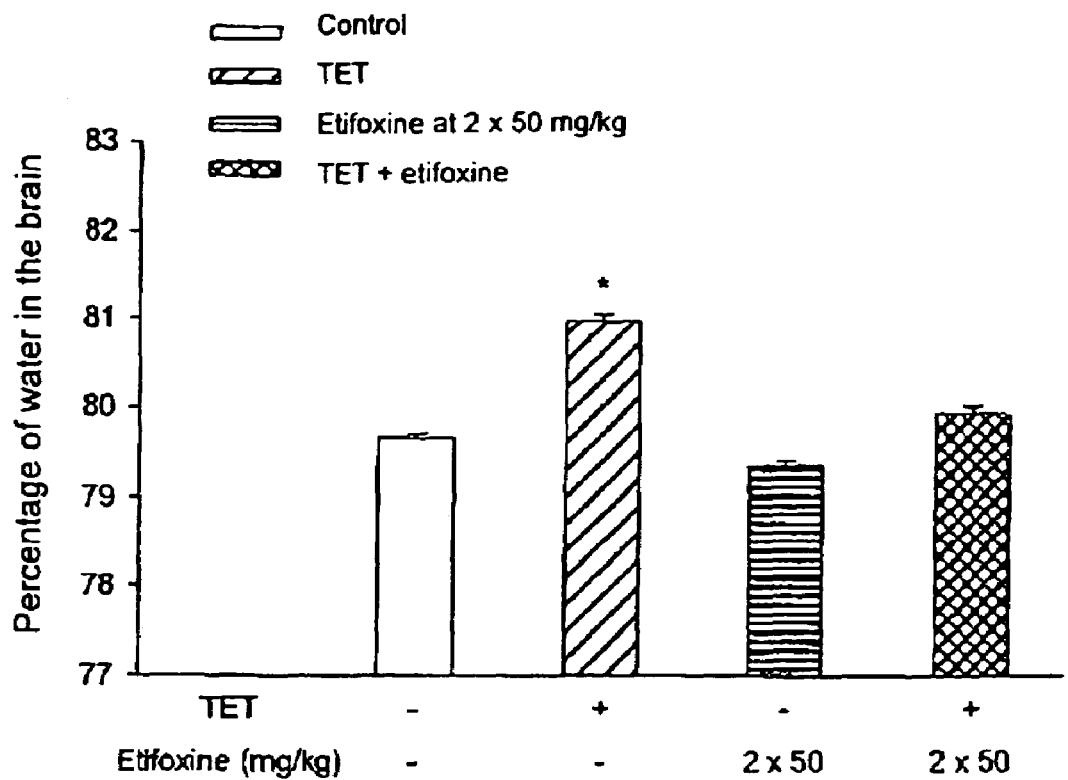
FIG. 1A, FIG. 1B
Figure 1B:
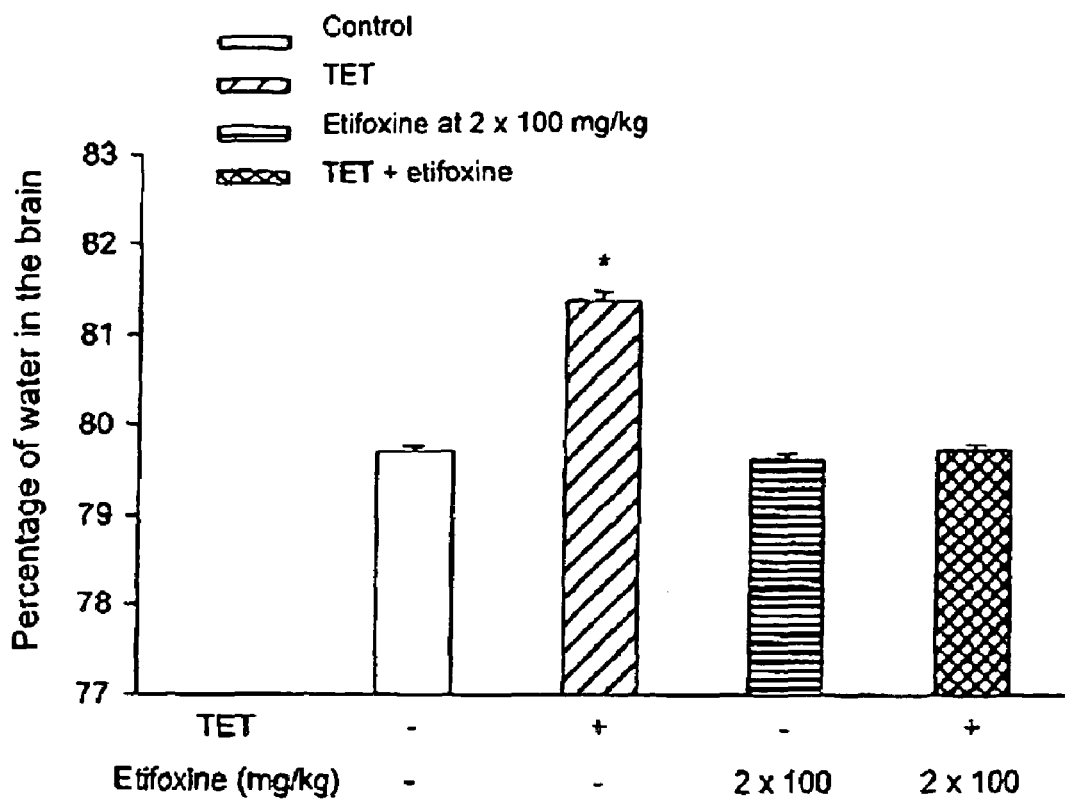

The administration of etifoxine alone at 2×50 or 2×100 mg/kg/d for 5 days does not modify the percentage of water in the brain in the rat (Table 1 and FIGS. 1A, 1B).

TET at 3 mg/kg/d, for 5 days, leads to a significant increase in the percentage of water, from 79.65% and 79.70%, respectively, for the two control groups, to 80.96% and 81.37%, respectively, for the two treated groups, indicating the presence of a cerebral oedema.

The concomitant administration of etifoxine at 2×50 mg/kg/d and of TET suppresses the significant increase in the percentage of water induced by TET. Likewise, at a dose of 2×100 mg/kg/d, etifoxine inhibits the effect of TET on the percentage of water.

On the other hand, the weight of the dried brain is 281 mg and 278 mg, respectively, in the control groups. TET or etifoxine administered on their own, or administered together, do not modify this parameter significantly.

Body Weight

At the level of the development of the body weight of the rats, TET brings about a significant drop in weight at d4 (Table 2 and FIGS. 2A, 2B).

Etifoxine administered on its own at 2×50 mg/kg/d does not disrupt weight gain. At a dose of 2×100 mg/kg/d, etifoxine brings about a significant reduction in the body weight of the rats at d3 and d4 as compared with the control groups, but the fall is not as great as with TET.

In the presence of TET and etifoxine at 2×50 mg/kg/d, it is noted that the body weight of the rats at d4 has not fallen as much as that of the group receiving TET on its own, and the difference is no longer significant relative to the control group. In that case, etifoxine partly prevents the drop in weight induced by TET.

In the presence of TET and etifoxine at 2×100 mg/kg/d, it is noted that the drop in weight observed at d4 in the group receiving only TET does not occur. Etifoxine therefore appears to reduce the drop in weight induced by TET.

Neurological Index

The administration of etifoxine at 2×50 or 2×100 mg/kg/d for 5 days does not lead to any behavioural sign in the rat (Table 3 and FIGS. 3A, 3B).

TET at 3 mg/kg/d, for 5 days, leads to a significant increase in the neurological index from d3, with a much stronger effect at d4, indicating substantial neurological troubles.

The concomitant administration of etifoxine at 2×50 mg/kg/d and of TET inhibits the increase in the neurological index at d3 and reduces it considerably at d4.

At a dose of 2×100 mg/kg/d, etifoxine inhibits the effect of TET on the neurological index completely.

Ambulatory Activity

The appropriate administration of etifoxine at 2×50 mg/kg/d or 2×100 mg/kg/d for 5 days does not lead to any significant effect on the ambulatory activities in the rat (Tables 4 and 5 and FIGS. 4A, 4B, 4C, 5A, 5B, 5C).

TET at 3 mg/kg/d, for 5 days, leads to a pronounced decrease in the ambulatory activities at d4, with almost total inhibition of vertical ambulatory activity.

The concomitant administration of etifoxine at 2×50 mg/kg/d and of TET does not suppress the effect of TET, but reduces it partially at the level of vertical ambulatory activity. At a dose of 2×100 mg/kg/d, etifoxine inhibits the effect of TET completely at the level of total and horizontal ambulatory activity and reduces it considerably at the level of vertical ambulatory activity.

2.3. Effect of Desethyl-Etifoxine

Cerebral Oedema

The administration of desethyl-etifoxinealone alone at 2×50 mg/kg/d for 5 days does not modify the percentage of water in the brain in the rat (Table 6 and FIG. 6).

TET at 3 mg/kg/d, for 5 days, leads to a significant increase in the percentage of water, from 79.85% to 81.29%, indicating the presence of a cerebral oedema.

The concomitant administration of desethyl-etifoxine at 2×50 mg/kg/d and of TET suppresses the significant increase in the percentage of water induced by TET.

On the other hand, the weight of the dried brain is 267±3 mg in the control group.

TET or desethyl-etifoxine, administered independently or administered together, do not modify this parameter significantly.

Body Weight

At the level of the development of the body weight of the rats, TET brings about a significant drop in weight at d4 (Table 7 and FIG. 7).

Desethyl-etifoxine administered on its own at 2×50 mg/kg/d does not disrupt the weight gain.

In the presence of TET and of desethyl-etifoxine at 2×50 mg/kg/d, it is noted that the body weight of the rats at d4 has not decreased relative to the control group. Desethyl-etifoxine prevents the drop in body weight induced by TET.

Neurological Index

The appropriate administration of desethyl-etifoxine at 2×50 mg/kg/d for 5 days does not lead to any behavioural sign in the rat (Table 8 and FIG. 8).

TET at 3 mg/kg/d, for 5 days, leads to a significant increase in the neurological index from d3, with a much stronger effect at d4, indicating substantial neurological troubles.

The concomitant administration of desethyl-etifoxine at 2×50 mg/kg/d and of TET inhibits the increase in the neurological index at d3 and at d4.

Ambulatory Activity

The administration of desethyl-etifoxine alone at 2×50 mg/kg/d for 5 days does not lead to any significant effect on the ambulatory activities in the rat (Table 9 and FIGS. 9A, 9B, 9C).

TET at 3 mg/kg/d, for 5 days, leads to a pronounced decrease in the ambulatory activities at d4, with almost total diminution of vertical ambulatory activity.

The concomitant administration of desethyl-etifoxine at 2×50 mg/kg/d and of TET suppresses the effect of TET completely.

TABLE 1

Effect of etifoxine on cerebral oedema induced by triethyl tin (TET), by measuring the percentage of water in the brain, in the rat (n = 10). The rat receives, orally for 5 days, etifoxine twice daily and TET at 3 mg/kg/d. On the 5th day, the brain is removed and then dried for 72 hours at 90° C., in order to determine the percentage of water present in the brain.

| TET (mg/kg/d) | Etifoxine (mg/kg/d) | Percentage of water (mean ± s.e.m.) | Variation in percentage | ANOVA statistical test |
|---|---|---|---|---|
| 0 | 0 | 79.65 ± 0.05 | | |
| 3 | 0 | 80.96 ± 0.07 | +1.31 | $p < 0.05$ |
| 0 | 2 × 50 | 79.35 ± 0.05 | −0.30 | ns |
| 3 | 2 × 50 | 79.92 ± 0.08 | +0.27 | ns |
| 0 | 0 | 79.70 ± 0.07 | | |
| 3 | 0 | 81.37 ± 0.10 | +1.67 | $p < 0.05$ |
| 0 | 2 × 100 | 79.63 ± 0.07 | −0.07 | ns |
| 3 | 2 × 100 | 79.72 ± 0.07 | +0.02 | ns |

TABLE 2

Effect of etifoxine on the development of body weight disrupted by triethyl tin (TET) in the rat (n = 10). Starting from d 0, the rat receives, orally for 5 days, etifoxine twice daily and TET at 3 mg/kg/d.

| TET (mg/kg/d) | Etifoxine (mg/kg/d) | Body weight in grams (mean ± s.e.m.) | | | | | |
|---|---|---|---|---|---|---|---|
| | | d −3 | d 0 | d 1 | d 2 | d 3 | d 4 |
| 0 | 0 | 224 ± 4 | 252 ± 4 | 259 ± 4 | 266 ± 4 | 273 ± 5 | 281 ± 4 |
| 3 | 0 | 222 ± 4 | 250 ± 5 | 253 ± 5 | 260 ± 5 | 262 ± 6 | 255 ± 7 * |
| 0 | 2 × 50 | 223 ± 4 | 251 ± 4 | 258 ± 3 | 267 ± 3 | 274 ± 4 | 282 ± 4 |
| 3 | 2 × 50 | 220 ± 3 | 248 ± 3 | 249 ± 3 | 257 ± 3 | 262 ± 3 | 268 ± 4 |
| 0 | 0 | 214 ± 2 | 242 ± 2 | 249 ± 3 | 254 ± 3 | 262 ± 3 | 270 ± 3 |
| 3 | 0 | 218 ± 2 | 246 ± 3 | 249 ± 3 | 254 ± 3 | 255 ± 4 * | 240 ± 4 * |
| 0 | 2 × 100 | 209 ± 2 | 234 ± 2 | 238 ± 2 | 245 ± 4 | 251 ± 3 * | 258 ± 3 * |
| 3 | 2 × 100 | 213 ± 2 | 242 ± 2 | 246 ± 2 | 248 ± 4 | 251 ± 4 | 257 ± 4 * |

(* $p < 0.05$ by an ANOVA statistical test in order to compare the treated groups with the group without treatment).

TABLE 3

Effect of etifoxine on the neurological index disrupted by triethyl tin (TET) as a function of time, in the rat (n = 10). Starting from d 0, the rat receives, orally for 5 days, etifoxine twice daily and TET at 3 mg/kg/d.

| TET (mg/kg/d) | Etifoxine (mg/kg/d) | Neurological index (means ± s.e.m.) | | | | | |
|---|---|---|---|---|---|---|---|
| | | d −3 | d 0 | d 1 | d 2 | d 3 | d 4 |
| 0 | 0 | 0 | 0 | 0 | 0 | 0 | 0 |
| 3 | 0 | 0 | 0 | 0 | 0 | 0.80 ± 0.23 * | 2.25 ± 0.11 * |
| 0 | 2 × 50 | 0 | 0 | 0 | 0 | 0 | 0 |
| 3 | 2 × 50 | 0 | 0 | 0 | 0 | 0.15 ± 0.11 * | 0.55 ± 0.20 * |
| 0 | 0 | 0 | 0 | 0 | 0 | 0 | 0 |
| 3 | 0 | 0 | 0 | 0 | 0 | 1.35 ± 0.15 * | 2.65 ± 0.08 * |
| 0 | 2 × 100 | 0 | 0 | 0 | 0 | 0 | 0 |
| 3 | 2 × 100 | 0 | 0 | 0 | 0 | 0.10 ± 0.07 * | 0.10 ± 0.07 * |

(* $p < 0.05$, ANOVA statistical test relative to the respective control groups).
Neurological index:
0 → no apparent anomaly
1 → loss of spontaneous activity: the rat does not leave a limited surface within a period of 60 seconds, but it escapes therefrom normally if it is stimulated (noise, pinching); it has lost its exploratory activity but retains its motor capacities
2 → loss of the gripping reflex when the rat is pushed against the surface
3 → loss of the retreat reflex, coma followed in the majority of cases by death

TABLE 4

Effect of etifoxine on ambulatory activity (arbitrary unit) disrupted by triethyl tin (TET) in the rat (n = 10). The rat receives, orally for 5 days, etifoxine twice daily and TET at 3 mg/kg/d. Measurements are carried out at d −3, before any treatment, and at d4, at the end of the study.

| TET (mg/kg/d) | Etifoxine (mg/kg/d) | d −3 (mean ± s.e.m.) | d4 (mean ± s.e.m.) |
|---|---|---|---|
| TOTAL AMBULATORY ACTIVITY | | | |
| 0 | 0 | 3758 ± 537 | 2569 ± 204 |
| 3 | 0 | 3859 ± 333 | 1208 ± 195 * |
| 0 | 2 × 50 | 3660 ± 212 | 2434 ± 346 |
| 3 | 2 × 50 | 3260 ± 196 | 1339 ± 226 * |
| HORIZONTAL AMBULATORY ACTIVITY | | | |
| 0 | 0 | 2964 ± 467 | 1925 ± 187 |
| 3 | 0 | 3028 ± 273 | 405 ± 80 * |
| 0 | 2 × 50 | 2874 ± 202 | 2018 ± 223 |
| 3 | 2 × 50 | 2429 ± 159 | 934 ± 180 * |
| VERTICAL AMBULATORY ACTIVITY | | | |
| 0 | 0 | 391 ± 80 | 250 ± 33 |
| 3 | 0 | 348 ± 49 | 7 ± 3 * |
| 0 | 2 × 50 | 322 ± 40 | 268 ± 39 |
| 3 | 2 × 50 | 281 ± 23 | 98 ± 23 * |

(* $p < 0.05$, ANOVA statistical test relative to the respective control groups).

TABLE 5

Effect of etifoxine on ambulatory activity (arbitrary unit) disrupted by triethyl tin (TET) in the rat (n = 10). The rat receives, orally for 5 days, etifoxine twice daily and TET at 3 mg/kg/d. Measurements are carried out at d −3, before any treatment, and at d4, at the end of the study.

| TET (mg/kg/d) | Etifoxine (mg/kg/d) | d −3 (mean ± s.e.m.) | d4 (mean ± s.e.m.) |
|---|---|---|---|
| TOTAL AMBULATORY ACTIVITY | | | |
| 0 | 0 | 2968 ± 353 | 2922 ± 276 |
| 3 | 0 | 2856 ± 320 | 1166 ± 114 * |
| 0 | 2 × 100 | 2950 ± 367 | 2345 ± 367 |
| 3 | 2 × 100 | 2659 ± 195 | 2174 ± 361 |
| HORIZONTAL AMBULATORY ACTIVITY | | | |
| 0 | 0 | 2310 ± 292 | 2269 ± 261 |
| 3 | 0 | 1839 ± 272 | 388 ± 71 * |
| 0 | 2 × 100 | 2195 ± 356 | 1714 ± 300 |
| 3 | 2 × 100 | 1998 ± 172 | 1650 ± 287 |
| VERTICAL AMBULATORY ACTIVITY | | | |
| 0 | 0 | 279 ± 48 | 331 ± 58 |
| 3 | 0 | 246 ± 48 | 2 ± 1 * |
| 0 | 2 × 100 | 284 ± 46 | 225 ± 39 * |
| 3 | 2 × 100 | 219 ± 20 | 162 ± 36 * |

(* $p < 0.05$, ANOVA statistical test relative to the respective control groups).

TABLE 6

Effect of desethyl-etifoxine on cerebral oedema induced by triethyl tin (TET), by measuring the percentage of water in the brain, in the rat (n = 10). The rat receives, orally for 5 days, desethyl-etifoxine twice daily and TET at 3 mg/kg/d. On the 5th day, the brain is removed and then dried for 72 hours at 90° C., in order to determine the percentage of water present in the brain.

| TET (mg/kg/d) | Desethyl-etifoxine (mg/kg/d) | Percentage of water (mean ± s.e.m.) | Variation in percentage | ANOVA statistical test |
|---|---|---|---|---|
| 0 | 0 | 79.85 ± 0.03 | | |
| 3 | 0 | 81.29 ± 0.07 | +1.44 | $p < 0.05$ |
| 0 | 2 × 50 | 79.76 ± 0.16 | −0.09 | ns |
| 3 | 2 × 50 | 80.24 ± 0.12 | +0.39 | ns |

TABLE 7

Effect of desethyl-etifoxine on the development of body weight disrupted by triethyl tin (TET) in the rat (n = 10). Starting from d 0, the rat receives, orally for 5 days, desethyl-etifoxine twice daily and TET at 3 mg/kg/d.

| TET (mg/kg/d) | Desethyl-etifoxine (mg/kg/d) | Body weight in grams (mean ± s.e.m.) | | | | | |
|---|---|---|---|---|---|---|---|
| | | d −3 | d 0 | d 1 | d 2 | d 3 | d 4 |
| 0 | 0 | 191 ± 2 | 217 ± 2 | 222 ± 3 | 228 ± 3 | 235 ± 3 | 242 ± 3 |
| 3 | 0 | 192 ± 3 | 216 ± 3 | 219 ± 3 | 223 ± 3 | 225 ± 4 | 210 ± 3 * |
| 0 | 2 × 50 | 193 ± 3 | 219 ± 3 | 224 ± 3 | 232 ± 3 | 240 ± 3 | 246 ± 3 |
| 3 | 2 × 50 | 194 ± 3 | 222 ± 3 | 226 ± 4 | 230 ± 4 | 238 ± 4 | 241 ± 3 |

(* $p < 0.05$ by an ANOVA statistical test in order to compare the treated groups with the group without treatment).

TABLE 8

Effect of desethyl-etifoxine on the neurological index disrupted by triethyl tin (TET) as a function of time, in the rat (n = 10). Starting from d 0, the rat receives, orally for 5 days, desethyl-etifoxine twice daily and TET at 3 mg/kg/d.

| TET (mg/kg/d) | Desethyl-etifoxine (mg/kg/d) | \multicolumn{6}{c}{Neurological index (means ± s.e.m.)} |
|---|---|---|---|---|---|---|---|
| | | d −3 | d 0 | d 1 | d 2 | d 3 | d 4 |
| 0 | 0 | 0 | 0 | 0 | 0 | 0 | 0 |
| 3 | 0 | 0 | 0 | 0 | 0 | 1.30 ± 0.13 * | 2.35 ± 0.13 * |
| 0 | 2 × 50 | 0 | 0 | 0 | 0 | 0 | 0 |
| 3 | 2 × 50 | 0 | 0 | 0 | 0 | 0.20 ± 0.13 * | 0.15 ± 0.08 |

(* $p < 0.05$, ANOVA statistical test relative to the respective control groups).
Neurological index:
0 → no apparent anomaly
1 → loss of spontaneous activity: the rat does not leave a limited surface within a period of 60 seconds, but it escapes therefrom normally if it is stimulated (noise, pinching); it has lost its exploratory activity but retains its motor capacities
2 → loss of the gripping reflex when the rat is pushed against the surface
3 → loss of the retreat reflex, coma followed in the majority of cases by death

TABLE 9

Effect of desethyl-etifoxine on ambulatory activity (arbitrary unit) disrupted by triethyl tin (TET) in the rat (n = 10). The rat receives, orally for 5 days, desethyl-etifoxine twice daily and TET at 3 mg/kg/d. Measurements are carried out at d −3, before any treatment, and at d4, at the end of the study.

| TET (mg/kg/d) | Desethyl-etifoxine (mg/kg/d) | d −3 (mean ± s.e.m.) | d4 (mean ± s.e.m.) |
|---|---|---|---|
| \multicolumn{4}{c}{TOTAL AMBULATORY ACTIVITY} | | | |
| 0 | 0 | 2558 ± 221 | 2606 ± 287 |
| 3 | 0 | 2782 ± 213 | 1445 ± 155 * |
| 0 | 2 × 50 | 2725 ± 364 | 2887 ± 423 |
| 3 | 2 × 50 | 2923 ± 210 | 2053 ± 256 |
| \multicolumn{4}{c}{HORIZONTAL AMBULATORY ACTIVITY} | | | |
| 0 | 0 | 1919 ± 171 | 1914 ± 224 |
| 3 | 0 | 2110 ± 181 | 601 ± 120 * |
| 0 | 2 × 50 | 2065 ± 298 | 2195 ± 355 |
| 3 | 2 × 50 | 2156 ± 182 | 1382 ± 222 |
| \multicolumn{4}{c}{VERTICAL AMBULATORY ACTIVITY} | | | |
| 0 | 0 | 259 ± 29 | 343 ± 43 |
| 3 | 0 | 320 ± 34 | 16 ± 7 * |
| 0 | 2 × 50 | 327 ± 57 | 475 ± 96 |
| 3 | 2 × 50 | 328 ± 47 | 295 ± 64 |

(* $p < 0.05$, ANOVA statistical test relative to the respective control groups).

The invention claimed is:

1. A method for treating cerebral oedema in an individual, comprising administering to said individual a prophylactically or therapeutically effective quantity of at least one compound of formula (II) below:

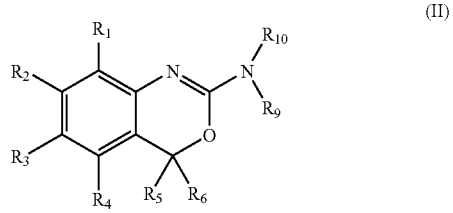

(II)

in which:
R$_1$, R$_2$, R$_3$ and R$_4$, which may be identical or different, represent a hydrogen atom, a halogen atom, especially selected from F, Cl, Br and I, a hydroxyl group, or an alkoxy group having 1 or 2 carbon atoms;
R$_5$ and R$_6$, which may be identical or different, represent a hydrogen atom, an alkyl or cycloalkyl group having from 1 to 6 carbon atoms, or an aryl group having 6 carbon atoms, the aromatic ring of which is optionally substituted by one or more halogen atoms or by one or more hydroxyl, alkoxy having 1 or 2 carbon atoms, trifluoromethyl or nitro groups;
R$_9$ and R$_{10}$, which may be identical or different, represent a hydrogen atom, a hydroxyl group, or an alkyl or hydroxyalkyl group having from 1 to 3 carbon atoms;
or a pharmaceutically acceptable salt thereof to thereby treat cerebral oedema.

2. The method of claim 1, wherein the compound is selected from the compounds of formulae (III) and (IV) below:

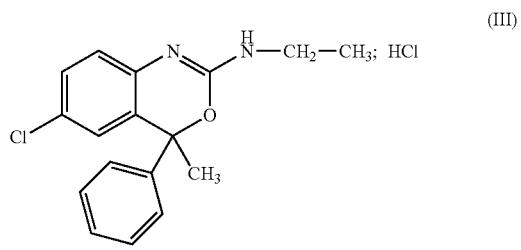

(III)

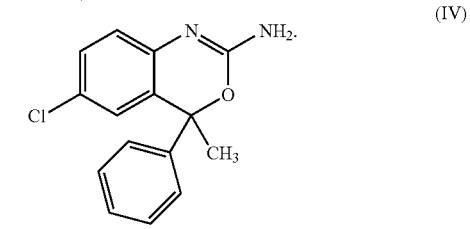

(IV)

3. The method of claim 1, wherein the cerebral oedema follows a cerebral vascular accident, a cerebral trauma, a cerebral tumour, cerebral metastases of a cancer, a cerebral abscess, a hypertensive attack, a diabetic ketoacidosis or a neuropaludism.

4. The method of claim 1, wherein the compound is administered to the individual at a unit dose of from approximately 50 mg to approximately 1500 mg, especially of from approximately 150 to 200 mg.

5. The method of claim 1, wherein the compound is administered to the individual at a dosage of approximately from 50 mg/day to approximately 1500 mg/day, especially approximately of from 150 mg/day to approximately 200 mg/day.

6. The method of claim 1, wherein the compound is administered by the oral route.

7. The method of claim 1, wherein the compound is administered in the form of a powder, tablets, capsules or sachets.

8. The method of claim 1, wherein the compound is administered simultaneously, separately, or sequentially with at least one additional compound for the treatment of cerebral oedema, such as a compound selected from the list comprising a corticoid, especially a glucocorticoid, glycerol, mannitol, a diuretic, especially furosemide, a barbiturate, tetracosactide, an antibiotic, CDP-choline, vinpocetine, a calcium inhibitor and a NMDA antagonist.

* * * * *

UNITED STATES PATENT AND TRADEMARK OFFICE
CERTIFICATE OF CORRECTION

PATENT NO. : 7,569,565 B2  Page 1 of 1
APPLICATION NO. : 11/488068
DATED : August 4, 2009
INVENTOR(S) : Le Guern et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 145 days.

Signed and Sealed this

Seventh Day of September, 2010

David J. Kappos
*Director of the United States Patent and Trademark Office*